(12) United States Patent
Clements et al.

(10) Patent No.: US 6,317,696 B1
(45) Date of Patent: Nov. 13, 2001

(54) APPARATUS AND METHOD FOR DETECTING FLUIDS

(75) Inventors: Jonathan Clements, Mirfield; Robert Chandler, Otley, both of (GB)

(73) Assignee: Bloodhound Sensors Limited, Leeds (GB)

( * ) Notice: Subject to any disclaimer, the term of this patent is extended or adjusted under 35 U.S.C. 154(b) by 0 days.

(21) Appl. No.: 09/171,771

(22) PCT Filed: Apr. 28, 1997

(86) PCT No.: PCT/GB97/01162

§ 371 Date: May 3, 1999

§ 102(e) Date: May 3, 1999

(87) PCT Pub. No.: WO97/41430

PCT Pub. Date: Nov. 6, 1997

(30) Foreign Application Priority Data

Apr. 27, 1996 (GB) .................................................. 9608774

(51) Int. Cl.[7] .................................................. G01N 11/00
(52) U.S. Cl. .................. 702/50; 702/12; 702/76; 702/100; 702/104; 73/1.02; 73/53.01
(58) Field of Search ................... 702/50, 76, 77, 702/104, 109, 12, 100; 73/25.01, 25.02, 25.03, 1.02, 53.01, 53.04, 23.2, 23.21, 24.06

(56) References Cited

U.S. PATENT DOCUMENTS

| 3,683,671 | * | 8/1972 | Van Swaay | 73/25.03 |
| 4,224,071 | | 9/1980 | Buell | 106/22 |

(List continued on next page.)

FOREIGN PATENT DOCUMENTS

| 0 332 935 A1 | 3/1989 | (EP) . |
| 0 358 249 A2 | 3/1990 | (EP) . |
| 2203553B | 10/1988 | (GB) | 27/12 |
| WO 94/29263 | 12/1994 | (WO) . |
| WO 86/01599 | 3/1986 | (WO) | 27/12 |

OTHER PUBLICATIONS

Nakata et al., New strategy for the development of a gas sensor based on the dynamic characteristics: principle and preliminary experiment, May 1992, Sensors and Actuators B. pp. 187–189.

*Primary Examiner*—Marc S. Hoff
*Assistant Examiner*—Hien Vo
(74) *Attorney, Agent, or Firm*—Beyer Weaver & Thomas LLP

(57) ABSTRACT

The present invention discloses an apparatus for detecting one or more fluids, the apparatus comprising a sensor means having electrical properties dependent upon one or more of the presence and the concentration of one or more fluids, an electrical excitation means for applying one or more electrical excitation pulses to the sensor means, a detector means for detecting the electrical behavior of the sensor means in response to the electrical excitation means, and a transformation means for transforming an output of the detector means from the time domain to the frequency domain to determine the electrical properties of the sensor means as a function of frequency over a pre-determined frequency range. The present invention also discloses a method of detecting one or more fluids, said method comprising applying one or more electrical excitation pulses to sensor means having electrical properties dependent upon one or more of the presence and the concentration of one or more fluids, detecting the electrical response of the sensor means to application of the or each said pulse, and transforming the detected response from the time domain to the frequency domain to provide the electrical characteristics of the sensor means as a function of frequency across a predetermined frequency range.

26 Claims, 2 Drawing Sheets

U.S. PATENT DOCUMENTS

| | | | |
|---|---|---|---|
| 4,399,684 | 8/1983 | Advani et al. | 73/1 G |
| 4,415,876 | 11/1983 | Yasuda et al. | 338/34 |
| 4,887,455 | 12/1989 | Payne et al. | 73/27 R |
| 5,034,192 | 7/1991 | Wrighton et al. | 422/82.02 |
| 5,672,515 * | 9/1997 | Furlong | 436/133 |

* cited by examiner

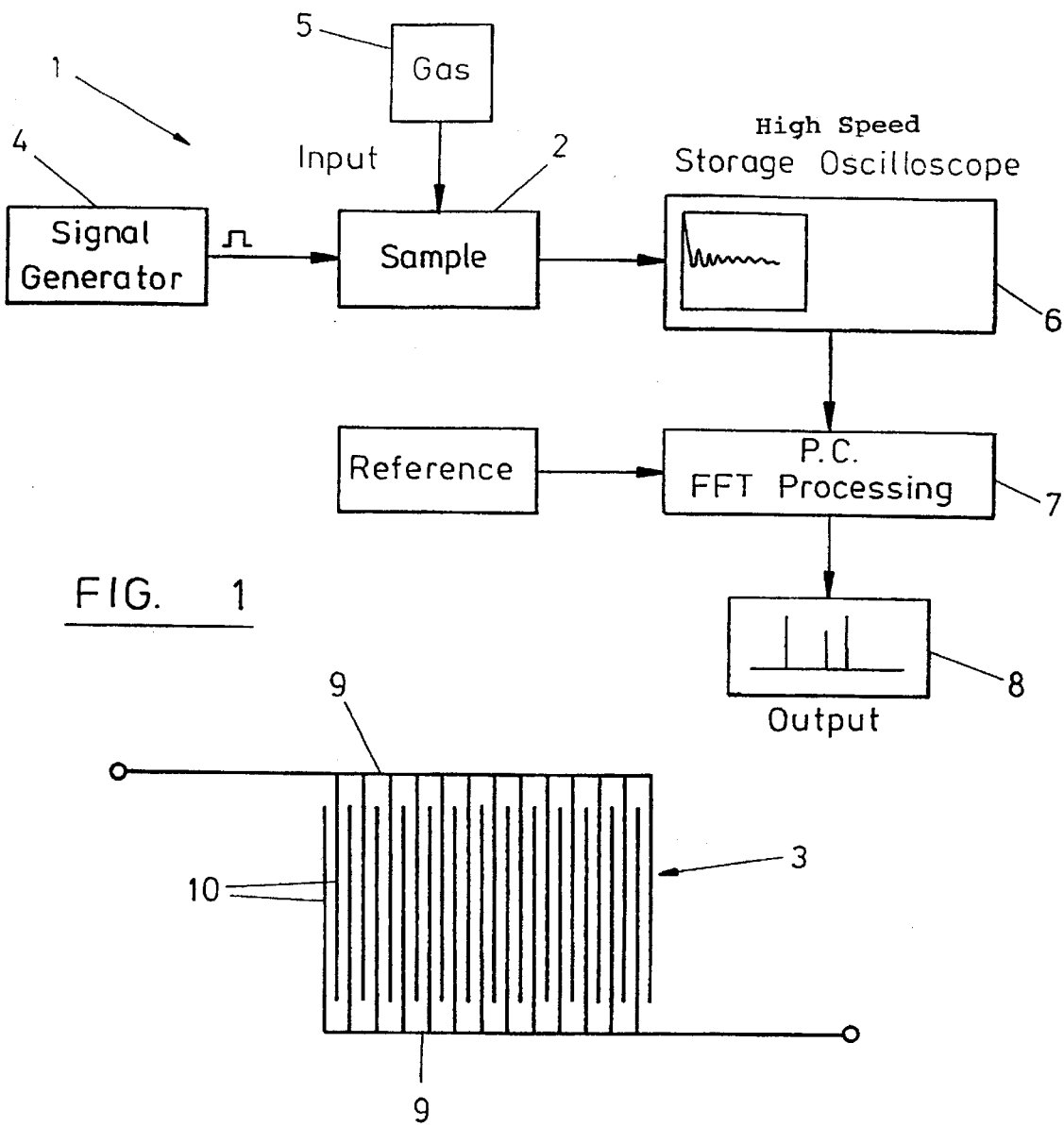
FIG. 1
FIG. 2
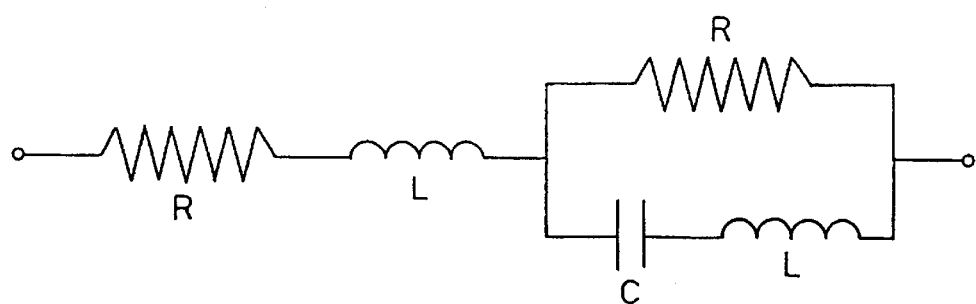
FIG. 3

APPARATUS AND METHOD FOR DETECTING FLUIDS

BACKGROUND OF THE INVENTION

FIELD OF THE INVENTION

The present invention relates to an apparatus and method for detecting fluids, and relates particularly to an apparatus and method for detecting fluids by observing the change in electrical behaviour of a sensor in the presence of such fluids. By "fluids" is meant samples of liquid and/or gas and/or vapour and combinations and/or mixtures of the same.

DESCRIPTION OF THE RELATED ART

Many materials are known to undergo changes in electrical behaviour in the presence of gases, primarily as a result of surface phenomena at the fluid/material interface, and which can be used to provide characteristic information to identify the gas causing the electrical change.

UK patent GB 2203553 discloses a gas sensor in which a layer of semi-conducting organic polymer such as polypyrrole is subjected to an alternating electrical signal in the frequency range 1 MHz to 500 MHz, and the frequency of which is then varied, and the variation in impedance characteristics of the organic polymer layer is obtained as a function of frequency in the presence of a gas to be detected. This variation in electrical behaviour as a function of frequency can then be used to identify the presence of a particular gas.

The above arrangement suffers from a number of drawbacks, including that the frequency scanning technique involved is time consuming, and the necessary hardware is expensive. In addition, although the exact mechanism by which the changes in electrical behaviour of the sensor are not fully understood, it is believed to result from many complex and interrelated factors which may vary throughout the course of the frequency scanning process, thus limiting the reproducibility of measurements, and which in turn may limit the accuracy with which gases may be detected.

Preferred embodiments of the present invention seek to overcome the above disadvantages of the prior art.

SUMMARY OF THE INVENTION

According to an aspect of the present invention, there is provided an apparatus for detecting one or more fluids, the apparatus comprising: sensor means having electrical properties dependent upon the presence and/or concentration of one or more fluids, excitation means for applying one or more excitation pulses to the sensor means, detector means for detecting the behaviour of the sensor means in response to the excitation means, and transforming means for transforming an output of the detector means from the time domain to the frequency domain to determine the electrical properties of the sensor means as a function of frequency over a pre-determined frequency range.

BRIEF DESCRIPTION OF THE DRAWINGS

A preferred embodiment of the present invention will now be described, by way of example only and not in any limitative sense, with reference to the accompanying drawings, in which:

FIG. 1 shows a gas sensor embodying the present invention;

FIG. 2 is a detailed view of a transducer of the apparatus of FIG. 1;

FIG. 3 is an equivalent electrical circuit to the transducer of FIG. 2;

DETAILED DESCRIPTION OF THE INVENTION

Figure 4:
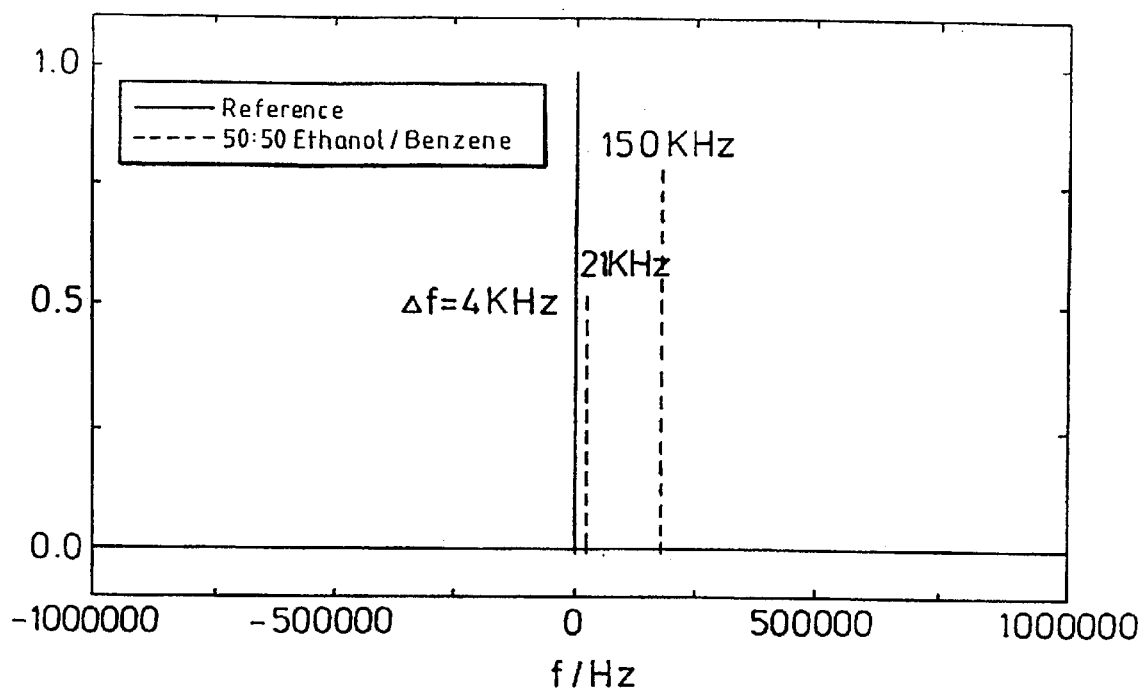
FIG. 4 shows a frequency spectrum obtained using the apparatus of FIG. 1.

According to an aspect of the present invention, there is provided an apparatus for detecting one or more fluids, the apparatus comprising: sensor means having electrical properties dependent upon the presence and/or concentration of one or more fluids, excitation means for applying one or more excitation pulses to the sensor means, detector means for detecting the behaviour of the sensor means in response to the excitation means, and transforming means for transforming an output of the detector means from the time domain to the frequency domain to determine the electrical properties of the sensor means as a function of frequency over a pre-determined frequency range.

By transforming an output of the detector means from the time domain to the frequency domain, this has the advantage of enabling the electrical properties of the sensor means to be determined over the entire predetermined frequency range much more rapidly than in the case of the prior art. In addition, although the exact mechanism causing changes in behaviour of the sensor means is not fully understood, it is believed that the absorption and desorption kinetics of the fluid in the sensor means provides useful characteristic information about the sample, and that a fast sampling speed is desirable to obtain this information. The present invention therefore provides the advantage that the faster sampling speed compared with the prior art enhances the quality of the information which may be derived.

In a preferred embodiment, the sensor means comprises one or more transducers, each of which comprises a pair of electrodes and one or more layers of material having electrical properties dependent upon the presence and/or concentration of one or more fluids.

The or each layer may comprise one or more of charge transfer complexes/electro-conductive salt composites, electro-conductive polymers and polymer composites, chemo-resistive semi-conductors, discotic liquid crystals, polymeric conductors and semi-conductors, piezo-electric materials, lipids, biological molecules, host/guest materials, porphyrins and related compounds, organo metallic materials, metallo organics, Langmuir Blodgett films, or amino acids.

The electrodes of the or each transducer may comprise a body portion having a plurality of projections interposed between corresponding projections of the other electrode.

By providing interposed (i.e. interdigitated) electrode projections, this has the advantage of providing a compact electrode pair construction at the same time as a large active surface area for both the electrode/sensor material and the sensor material/fluid interface, which in turn enables the resulting electrical change to be recorded with significantly improved signal to noise ratio than in the case of the prior art.

Said interposed electrodes may have a mutual separation of substantially 0.5 $\mu$m to substantially 50 $\mu$m.

In a preferred embodiment, the thickness of each said layer is up to substantially 1 $\mu$m.

The excitation means may provide one or more electrical pulses, each of which has a duration of substantially 1 $\mu$s to substantially 1 ms.

By providing one or more pulses of short duration, this has the advantage of enabling excitation of a sample across a broad frequency bandwidth.

In a preferred embodiment, the excitation means applies one or more first electrical pulses to the sensor means, and subsequently applies one or more second electrical pulses, the or each second pulse having a higher power and shorter duration than the or each first pulse.

This provides the advantage of enabling part of the spectrum of interest to be "pre-excited" at a selected frequency with a lower power long duration pulse, and then the entire spectrum to be observed by means of a higher power short duration pulse.

Furthermore, by providing short impulse electrical signals to the sensor means, the effects of oxidation, tracking and electrical breakdown within the sensor means are reduced.

In a preferred embodiment the excitation means applies a square wave pulse to the sensor means.

The transforming means preferably transforms from the time domain to the frequency domain by means of an integral transformation, and preferably by means of a linear integral transformation.

In an alternative embodiment the excitation pulse is electrical noise.

Preferably, the transformation is done by at least one of software or hardware.

By carrying out an integral transformation, this provides the advantage that an averaging method is used, which renders the apparatus less sensitive to asynchronous system noise.

In a preferred embodiment, the integral transformation is a Fourier transform.

The transforming means preferably transforms from the time domain to the frequency domain by means of a fast Fourier transform (FFT).

This provides the advantage that a convenient and well established method for obtaining a time domain to frequency domain transform can be used, and calculations can typically be carried out in less than a second after a single impulse signal is applied to the sensor means, thus offering considerable sampling speed advantages over the prior art. In addition, because of the wide availability of devices for carrying out fast Fourier transform (FFT) operations, the necessary transforms can be carried out conveniently and relatively inexpensively.

Preferably the transforming means transforms from the time domain to the frequency domain by means of a discreet fourier transform.

The apparatus preferably further comprises low pass filter means for removing high frequency components from the excitation means.

This provides the advantage of minimising errors which may arise as a result of aliasing which may arise in the fast Fourier transforming (FFT) operation.

The transforming means may apply a smoothing window to the output of the detection in real time to improve the spectral characteristics of the output. The window may be at least one of Blackman, Hanning or Hamming windows.

The apparatus preferably further comprises identification means for identifying one or more fluid components from the output of the transforming means.

According to another aspect of the invention, there is provided a method of detecting one or more fluids, the method comprising applying one or more excitation pulses to sensor means having electrical properties dependent upon the presence and/or concentration of one or more fluids, detecting the response of the sensor means to application of the or each said pulse, and transforming the detected response from the time domain to the frequency domain to provide the electrical characteristics of the sensor means as a function of frequency across a predetermined frequency range.

The method may comprise applying one or more first pulses to the sensor means, and subsequently applying one or more second pulses, each said second pulse having a higher power and shorter duration than the or each first pulse.

In a preferred embodiment, the transforming step comprises applying an integral transformation.

The integral transformation may be a linear integral transformation.

In a preferred embodiment, the integral transformation is a Fourier transform.

The transforming step is preferably carried out by means of a fast Fourier transform (FFT) algorithm.

The method preferably further comprises the step of low pass filtering higher frequency components of the input of the sensor means.

The method preferably further comprises the step of identifying one or more fluid components from the response of the sensor means transformed to the frequency domain.

Referring in detail to FIG. 1, a gas sensor 1 comprises a sample chamber 2 containing an array of transducers (not shown in FIG. 1), of which a single transducer 3 is shown in detail in FIG. 2, and respective inputs of which are connected to a signal generator 4. A gas inlet 5 is connected to the sample chamber 2 for supplying a gas sample to be identified, as well as one or more test gases to calibrate the apparatus 1.

The array of transducers 3 is connected to an input of a high speed storage oscilloscope 6, which detects the electrical output of the array of transducers 3 in the time domain. Each of the transducers 3 may be constructed to be responsive to the presence of a different gas. The output of oscilloscope 6 is input to a computer 7 which transforms the output of the oscilloscope from the time domain to the frequency domain by means of a fast fourier transform (FFT) algorithm, and thus provides an output at a suitable display 8 indicating the electrical characteristics of the transducers 3 as a function of frequency across a predetermined frequency range.

Referring to FIG. 2, each of the transducers 3 comprises a pair of electrodes 9 having interdigitated active elements 10 having a separation of generally 4 $\mu$m and coated with a thin film of thickness generally 0.5 $\mu$m, by suitable methods such as solution casting, of a material whose electrical behaviour (i.e. impedance) changes in the presence of one or more gases to be detected. The material in the present embodiment is the discotic liquid crystal 1-nitro 2,3,6,7,10, 11-hexa(hexyloxy)triphenylene (HAT 6-$NO_2$) having the following chemical formula:

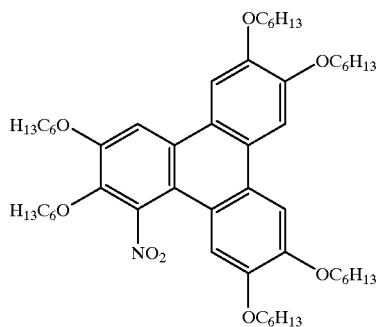

The discotic liquid crystal HAT 6-NO$_2$ is in its liquid crystalline phase at room temperature.

It can be seen from FIG. 2 that the electrical characteristics of the transducer 3 will have both resistive and capacitive features, which will contribute to the impedance of the gas sensor 1 as a whole, and both of which will change when the HAT 6-NO$_2$ layer, acting as a dielectric, is exposed to a gas to be detected. However, in the desorption stage, it is also believed that molecules desorb and reabsorb at different rates, which gives rise to inductive features. Accordingly, the transducer 3 of FIG. 2 can be represented by the equivalent electrical circuit shown in FIG. 3. Absorption and desorption of a gas in the sensor material will affect both the resistive and reactive (i.e. capacitive and inductive) components of the overall impedance characteristic of the sensor, which changes in electrical impedance result in a characteristic signature of a particular gas to be detected in both the time and frequency domain. Furthermore, the large active area of the sensor, and the relatively high resistance of the sensing material enable the device to be operated and interrogated at frequencies below 1 MHz, which, permits the use of an electronic sampling system having standard components and using low frequency techniques.

As will be understood by persons skilled in the art, in principle, any one of several integral transforms can be used to convert data collected in the time domain into the frequency domain for subsequent analysis. Examples of such integral transforms are Laplace transforms, Fourier transforms, Hankel transforms, Mellin transforms, Hartley transforms, Abel transforms, Hilbert transforms, Hardamard transforms, and Z transforms. Any arbitrary time domain excitation can be used to measure a system transfer function provided that the excitation is applied and the response recorded over a sufficiently long time to complete the transforms over the desired frequency band. Thus, in general, potential and current steps and pulses, such as square wave, saw tooth wave, triangular wave, and various noise excitations can all be used. Two stages of data manipulation are involved in obtaining the transfer function as a function of frequency from the response of the system to an arbitrary time domain perturbation, namely the input and response functions must be sampled and recorded in a time interval of interest, and then the transform of each must be computed and the complex ratio calculated.

It will also be appreciated by persons skilled in the art, that electrical pulses have the general property that although they may be driven by an oscillator at one particular frequency, they produce excitations across a range of frequencies, the band width of which is inversely proportional to the pulse duration. The transfer function of the sensor 1 in the presence of a gas to be detected can thus be determined quickly using a time domain technique followed by the application of a linear integral transformation correlation analysis by means of the computer 7. In the embodiment shown, this is carried out by means of fast Fourier transforms (FFT), since these are a convenient and well established method of obtaining a transform from the time domain to the frequency domain, and can typically be calculated in less than a second after a single impulse signal applied to the gas sensor. Furthermore, the use of linear integral transforms enables many elements of a system to be added and analysed simultaneously in the frequency domain, which in turn enables an assembly of one or more sensor materials that are response to different gases to be connected together on one or more electrodes to form an electronic analysis system. The resulting unique transfer function obtained from various reference fluids and sensors can then be stored and recorded digitally in the computer 7 for comparison with other reference or unknown samples.

The operation of the apparatus shown in FIGS. 1 and 2 will now be described.

A sample of gas to be analysed is input via gas inlet 5 to the sample chamber 2 so that the fluid sample is either in equilibrium with or dynamically flowing across the surface of each of the transducers 3. The signal generator 4 then applies a square pulse of 1 μs duration corresponding to an excitation band width of approximately 1 MHz, to the transducers 3. The electrical response of the array of transducers 3 is then detected and stored in high speed storage oscilloscope 6 and input to computer 7, in which the fast Fourier transform (FFT) algorithm is carried out.

The length of the fast Fourier transform (FFT) array of computer 7 is $2^n$ words, which in the above embodiment is 4096 words, and is collected over 10 ms. As a result, the lowest frequency accessible is 100 Hz, and the highest frequency for which complete phase and amplitude information is available is:

$$\frac{0.5 \times 4096}{0.01} = 204.8 \text{ KHz},$$

although it is possible to extend the frequency range to many more orders of magnitude, by applying the transformation to successive segments, The output of the computer 7 then provides the frequency domain response of the sensor 1 at display 8.

By means of a suitable correlation technique known to persons skilled in the art, such as fuzzy logic or an artificial intelligence algorithm, a predetermined degree of correlation between the frequency domain output of computer 7 and one or more reference values may be obtained to identify the presence and/or concentration of on e or more gases.

FIG. 4 shows a frequency spectrum of 50/50 ethanol benzene obtained using the apparatus 1 of FIGS. 1 and 2, from which it can be seen that two resonances occur in the spectrum due to the presence of the gas to be identified.

Figure 5:
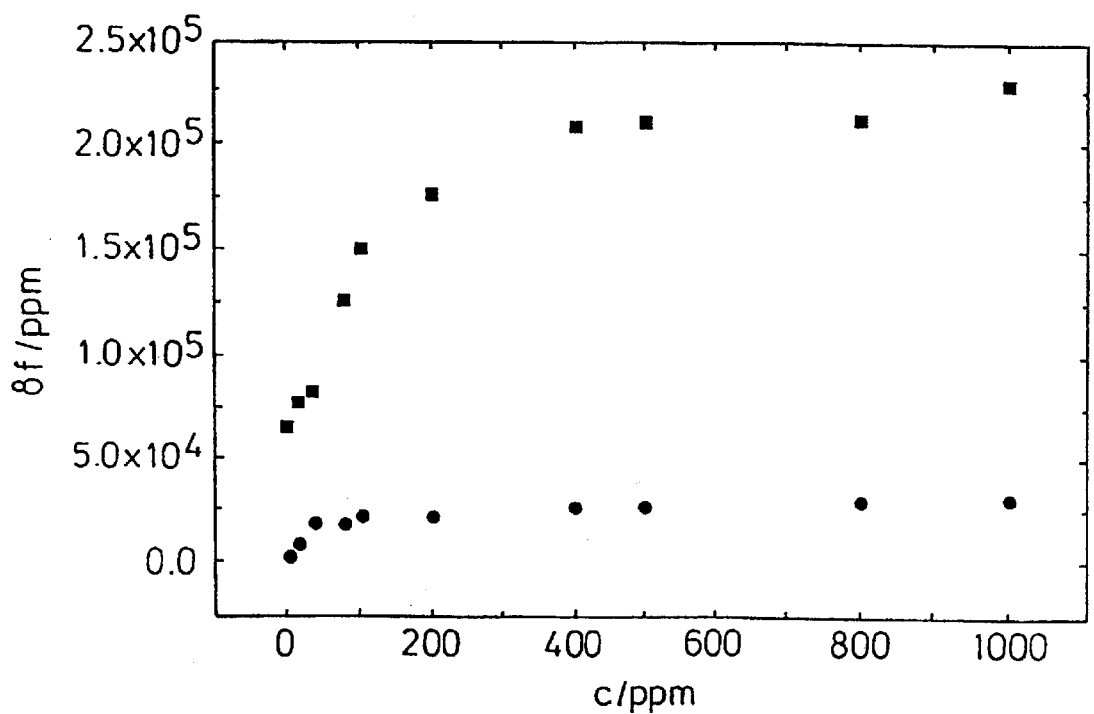
FIG. 5 is a graph of concentration dependence obtained using the apparatus of FIG. 1.

As shown in FIG. 5, the position of these two resonances is dependent upon concentration and the two peaks have very different concentration dependence. The magnitude of the resonances shown in FIG. 4, the absolute frequency shift and the ratio of change of the shift with concentration of the gas are all characteristic of the particular gas and can thus be used in its detection and identification.

As a result of the improved speed of sampling and reduced sensitivity to noise compared with the prior art, the apparatus 1 of FIGS. 1 and 2 can be used as part of a continuous monitoring process as part of a feedback control loop, for example in food and/or chemical production lines.

It will be appreciated by persons skilled in the art that the above embodiment has been described by way of example only, and not in any limitative sense, and that various alterations and modifications of the invention are possible without departure from the scope of the invention as defined by the appended claims. For example, the apparatus may detect liquids and liquid/gas mixtures as well as gases, and the excitation may occur by means of pulses other than electrical pulses, for example optical, mechanical, infra-red, acoustic, thermal or magnetic pulses.

What is claimed is:

1. An apparatus for detecting one or more fluids, the apparatus comprising: sensor means having electrical properties dependent upon one or more of the presence and the concentration of one or more fluids, electrical excitation means for applying one or more electrical excitation pulses to the sensor means, detector means for detecting the electrical behaviour of the sensor means in response to the electrical excitation means, and transforming means for transforming an output of the detector means from the time domain to the frequency domain to determine the electrical properties of the sensor means as a function of frequency over a pre-determined frequency range.

2. An apparatus according to claim 1, wherein the sensor means comprises one or more transducers, each of which further comprises a pair of electrodes and one or more layers of material having electrical properties dependent upon one or more of the presence and the concentration of the one or more fluids.

3. An apparatus according to claim 2, wherein the layer or the plurality of layers comprises one or more of charge transfer complexes/electro-conductive salt composites, electro conductive polymers and polymer composites, chemoresistive semi-conductors, discotic liquid crystals, polymeric conductors and semi-conductors, piezo-electric materials, lipids, biological molecules, host/guest materials, porphyrins and related compounds, organo metallic materials, metallo organics, Langmuir Blodgett films, or amino acids.

4. An apparatus according to claim 2, wherein the electrodes of the transducer or plurality of transducers comprise a body portion having a plurality of projections interposed between corresponding projections of the other electrode.

5. An apparatus according to claim 4, wherein said interposed electrodes preferably have a mutual separation of substantially 0.5 $\mu$m to substantially 50 $\mu$m.

6. An apparatus according to claim 2, wherein the thickness of each said layer is up to substantially 1 $\mu$m.

7. An apparatus according to claim 1, wherein the excitation means provides one or more electrical pulses, each of which has a duration of substantially 1 $\mu$s to substantially 1 ms.

8. An apparatus according to claim 1, wherein the excitation means applies one or more first electrical pulses to the sensor means, and subsequently applies one or more second electrical pulses, the or each second pulse having a higher power and shorter duration than the or each first pulse.

9. An apparatus according to claim 1, wherein the transforming means transforms from the time domain to the frequency domain by means of an integral transformation.

10. An apparatus according to claim 9, wherein the transformation is a linear integral transformation.

11. An apparatus according to claim 9, wherein the integral transformation is a Fourier transform.

12. An apparatus according to claim 11, wherein the transforming means transforms from the time domain to the frequency domain by means of a fast Fourier transform (FFT).

13. An apparatus according to claim 1, further comprising low pass filter means for removing high frequency components from the excitation means.

14. An apparatus according to claim 1, further comprising identification means for identifying one or more fluid components from the output of the transforming means.

15. A method of detecting one or more fluids, the method comprising applying one or more electrical excitation pulses to sensor means having electrical properties dependent upon one or more of the presence and the concentration of one or more fluids, detecting the electrical response of the sensor means to application of the or each said pulse, and transforming the detected response from the time domain to the frequency domain to provide the electrical characteristics of the sensor means as a function of frequency across a predetermined frequency range.

16. A method according to claim 15, comprising applying one or more first pulses to the sensor means, and subsequently applying one or more second pulses, each said second pulse having a higher power and shorter duration than the or each first pulse.

17. A method according to claim 15, wherein the transforming step comprises applying an integral transformation.

18. A method according to claim 17, wherein the transformation is a linear integral transformation.

19. A method according to claim 17, wherein the integral transformation is a Fourier transform.

20. A method according to claim 19, wherein the transforming step is preferably carried out by means of a fast Fourier transform (FFT) algorithm.

21. A method according to claim 15, further comprising the step of low pass filtering higher frequency components of the input of the sensor means.

22. A method according to claim 15, further comprising the step of identifying one or more fluid components from the response of the sensor means transformed to the frequency domain.

23. An apparatus for detecting one or more fluids, the apparatus comprising: sensor means having electrical properties dependent upon one or more of the presence and the concentration of one or more fluids; excitation means for applying an excitation to the sensor means, wherein said excitation means comprises a broad band electrical noise; detector means for detecting the behaviour of the sensor means in response to the excitation means, and transforming means for transforming an output of the detector means from the time domain to the frequency domain to determine the electrical properties of the sensor means as a function of frequency over a pre-determined frequency range, wherein said excitation comprises a broad band electrical noise.

24. A method of detecting one or more fluids, the method comprising: applying an excitation to sensor means having electrical properties dependent upon one or more of the presence and the concentration of one or more fluids; detecting the response of the sensor means to application of the excitation; and transforming the detected response from the time domain to the frequency domain to provide the electrical characteristics of the sensor means as a function of predetermined frequency range.

25. A method as in claim 24 wherein said excitation comprises a broad band electrical noise.

26. A method as in claim 25 wherein said electrical noise excitation comprises at least one pulse.

* * * * *